United States Patent
Müller et al.

(10) Patent No.: US 9,511,646 B2
(45) Date of Patent: Dec. 6, 2016

(54) SEAT ASSEMBLY WITH TEMPERATURE OR HUMIDITY SENSOR

(71) Applicant: Sensirion AG, Stäfa (CH)

(72) Inventors: Christoph Müller, Stäfa (CH); Michael Götze, Stäfa (CH); Markus Graf, Stäfa (CH)

(73) Assignee: Sensirion AG, Stäfa (CH)

( * ) Notice: Subject to any disclaimer, the term of this patent is extended or adjusted under 35 U.S.C. 154(b) by 0 days.

(21) Appl. No.: 14/629,853

(22) Filed: Feb. 24, 2015

(65) Prior Publication Data
US 2015/0239321 A1 Aug. 27, 2015

(30) Foreign Application Priority Data

Feb. 25, 2014 (EP) .................................. 14156631

(51) Int. Cl.
| | | |
|---|---|---|
| *B60N 2/56* | (2006.01) | |
| *B60H 1/00* | (2006.01) | |
| *B60N 2/58* | (2006.01) | |
| *G01N 19/10* | (2006.01) | |

(52) U.S. Cl.
CPC ............. *B60H 1/00792* (2013.01); *B60N 2/56* (2013.01); *B60N 2/58* (2013.01); *G01N 19/10* (2013.01)

(58) Field of Classification Search
CPC ........... B60N 2/5678; B60N 2/56; B60N 2/05; B60N 2/08; A47C 7/74; A47C 7/742; A47C 7/748; G01N 19/10; B60H 1/00792
See application file for complete search history.

(56) References Cited

U.S. PATENT DOCUMENTS

| | | | | |
|---|---|---|---|---|
| 6,469,303 B1 * | 10/2002 | Sun | .................... | G01N 21/3504 250/338.3 |
| 7,362,225 B2 * | 4/2008 | Rittmueller | ......... | B60R 21/0152 324/207.15 |
| 7,506,924 B2 * | 3/2009 | Bargheer | ............. | B60N 2/4876 297/180.14 |
| 7,791,476 B2 * | 9/2010 | Hawkins | ................ | B60N 2/002 340/561 |
| 2003/0214160 A1* | 11/2003 | Brennan | .................. | A47C 7/74 297/180.14 |
| 2006/0175877 A1* | 8/2006 | Alionte | .................... | A47C 7/74 297/180.14 |
| 2007/0241895 A1* | 10/2007 | Morgan | ................. | B60N 2/002 340/561 |

(Continued)

FOREIGN PATENT DOCUMENTS

| | | |
|---|---|---|
| DE | 102 55 441 B3 | 4/2004 |
| DE | 10255441 * | 4/2004 |

(Continued)

OTHER PUBLICATIONS

Search report dated Jul. 10, 2014 in European application No. 14156631 (5 pgs.)

*Primary Examiner* — Philip Gabler
(74) *Attorney, Agent, or Firm* — Foley & Lardner LLP

(57) ABSTRACT

A sensor module for integration within a seat assembly is provided. The sensor module comprises a temperature and/or humidity sensor (21) and a separate sensor support (51) for mechanically supporting said temperature and/or humidity sensor. The sensor support is configured to be arranged on or in a support layer below an air-permeable cover of the seat assembly.

37 Claims, 5 Drawing Sheets

(56) References Cited

U.S. PATENT DOCUMENTS

2009/0033130 A1\* 2/2009 Marquette ............... A47C 7/74
 297/180.15

FOREIGN PATENT DOCUMENTS

| DE | 10 2006 017732 A1 | 10/2007 |
| DE | 10 2007 031 322 B3 | 10/2008 |
| EP | 2 607 155 A1 | 6/2013 |
| FR | 2 630 056 A1 | 10/1989 |
| GB | 2 343 747 A | 5/2000 |
| JP | H07-49142 A | 2/1995 |
| WO | WO 02/06083 A1 | 1/2002 |
| WO | WO 02/053411 A2 | 7/2002 |

\* cited by examiner

SEAT ASSEMBLY WITH TEMPERATURE OR HUMIDITY SENSOR

CROSS REFERENCED TO RELATED APPLICATIONS

This application claims priority to European Patent Office application no. 14156631 filed Feb. 25, 2014, the entire contents of which are incorporated by reference herein.

TECHNICAL FIELD

The present invention relates to a sensor module for integration within a seat assembly and to a corresponding seat assembly. The seat assembly can be, in particular, a vehicle seat or a part thereof.

PRIOR ART

Ventilated vehicle seats are known in the art, e.g. from WO 02/053411 A2, FR 2 630 056, U.S. Pat. No. 7,506,924 B2, EP 2 607 155 A1 or DE 10 2007 031 322 B3. Such seats can improve occupant comfort by forcing air through the seat. The air can be simply drawn from the ambient air within the vehicle cabin, or it can be cooled and/or heated. In the latter case, dedicated cooling and/or heating systems inside the seat can be employed, or the seat can be coupled to an air conditioning system for the vehicle cabin. Common systems use conduits within the seat and an air-permeable seat cover to provide ventilated air, which may be heated or cooled, to the occupant by pushing air through the seat cover. Other systems pull air through the seat cover.

In known systems the user can control the air flow by increasing or decreasing the total flow. For example, a user interface may provide settings "low", "medium" and "high". If the seat is actively cooled or heated, the occupant may in addition manually set the cooling or heating power. However, the chosen setting might not always be the optimum system setting in view of comfort and energy consumption.

JP H07-49142A discloses a ventilated seat that employs humidity sensors and temperature sensors to detect a physiological state of the occupant of the seat. By employing such sensors, some of the disadvantages of manual control of the settings can be overcome. However, the document does not give details about the manner in which the sensors are mounted to the seat.

SUMMARY OF THE INVENTION

It is an object of the present invention to provide a sensor module comprising a temperature and/or humidity sensor that can readily be mounted in a seat in such a manner the sensor readings adequately reflect the physiological condition of the occupant, that the sensor does not negatively impact the aesthetic appearance of the seat, and that the sensor is adequately protected from mechanical stress.

The sensor module is configured to be integrated within a seat assembly comprising a seat bottom and a backrest. The seat bottom will normally define a generally horizontal seating surface. The seat bottom is commonly also referred to as a "cushion" in the automotive art. The backrest will generally be coupled to the seat bottom and arranged to extend in an upward direction away from the seat bottom to support the back of a seated occupant. At least one of the seat bottom and the backrest comprises an air-permeable cover and a support layer (e.g., a foam layer or a fiber-based layer like a fiber mat, a backing layer, or any other functional layer such as a heating mat that directly or indirectly provides some kind of support to the air-permeable cover). The air-permeable cover has an outside surface, which forms an occupant contact area of the seat assembly, and an inside surface. Further layers may be present. The sensor module comprises a temperature and/or humidity sensor and a separate sensor support for mechanically supporting the temperature and/or humidity sensor, the sensor support being configured to be arranged on or in the support layer below the air-permeable cover.

By placing the sensor module below the inside surface of the air-permeable cover, humidity (which primarily results from perspiration of the occupant) and temperature, as measured by the sensor module, adequately reflect the physiological condition of the occupant (such as sweat level and skin temperature) with short response times. At the same time, the sensor module is protected from view and from dirt. The sensor module comprises the sensor itself, which will generally comprise an integral packaging, and a separate sensor support. By providing a separate sensor support in addition to the packaging of the sensor itself, the sensor is protected from mechanical stress due to the presence of the occupant. By arranging the sensor support on or in the support layer, the sensor module does not overly disturb the occupant.

The sensor module comprises a temperature and/or humidity sensor. In particular, the sensor can be a combined temperature and humidity sensor. However, it is also conceivable that the sensor module comprises only a temperature sensor or only a humidity sensor. The sensor can in addition be sensitive to further parameters other than temperature and humidity.

The sensor can have an active sensor surface, i.e., a surface portion of the sensor that is primarily sensitive to the parameter of interest. In the case of a semiconductor-based humidity sensor, the active sensor surface is usually a sensitive layer, e.g. a polymer layer, on a semiconductor substrate. In many cases, the active sensor surface has a well-defined surface normal. The active sensor surface can have arbitrary orientation. However, it is preferred that the active sensor surface faces the inside surface of the air-permeable cover. In particular, it is preferred that the active sensor surface is parallel to the air-permeable cover.

In order to provide optimal mechanical protection of the sensor, the sensor support can define a window that is fully surrounded by the material of which the sensor support is made, and the temperature and/or humidity sensor can be disposed below the window. In some embodiments, in particular, in the case of some semiconductor sensors, the active sensor surface is accessible to media through a window-like opening of the packaging of the sensor itself, i.e., the active sensor surface can be disposed below the window-like opening, or at least a diffusion path exists between the active sensor surface and the environment through the window-like opening. In such cases, there are two windows to provide access for media to the active sensor surface: the first window is provided in the packaging of the sensor itself, the packaging providing a first contribution to mechanical protection. The second window is provided in the separate sensor support. The sensor support provides a second contribution to mechanical protection of the sensor. The two windows can be arranged on top of one another; however this is not necessary as long as a diffusion path exists through the windows to the active sensor surface.

In order to protect the active sensor surface from dirt and liquids, such as accidentally spilled liquids or cleaning agents, the sensor module can comprise an air-permeable protective membrane that covers the active sensor surface. Preferably the protective membrane is attached to the sensor support to cover the window of the sensor support. In this manner the membrane can be easily secured to the sensor module, and a well-defined distance between the membrane and the active sensor surface can be maintained.

The sensor support can be rigid or flexible, or it can have rigid and flexible portions interconnected to one another. The sensor support can include a rigid or flexible base portion that has an essentially planar bottom surface configured to rest flat on the support layer. The base portion can be fixedly connected to the support layer by the use of an adhesive (i.e. it can be glued to the support layer). To this end, the bottom surface of the base portion can be provided with an adhesive layer. The adhesive layer can be covered by a removable, in particular, peelable, protective layer that can be removed before the sensor module is attached to the support layer. The adhesive layer can be supported by a backing layer, which is attached to the bottom surface of the base portion by means of another adhesive layer. In particular, the bottom surface of the sensor support may be provided with a double-sided adhesive tape, in order to provide a sensor module that is ready to mount.

The sensor support can include one or more rigid anchors that are configured to extend from the base portion into the support layer when the base portion rests flat on the support layer. In some embodiments, these anchors can be configured to pierce the support layer without the need of forming pre-formed cavities in the support layer to receive the anchors. To this end, the anchors may have an elongated shaped, preferably a pointed shape, i.e., a shape that tapers towards the free end of the anchor, and may have lateral dimensions perpendicular to the longitudinal direction of the anchor that are smaller than 10 mm, preferably 5 mm. In other embodiments, the anchors can be configured to be received in pre-formed cavities of the support layer. The anchors can be provided in addition to an adhesive layer or instead of an adhesive layer as discussed above.

Preferably the entire top surface of the sensor module that is configured to face away from the support layer towards the air-permeable cover is essentially flat and devoid of any prominent protrusions. It is preferred that the top surface is domed. If the sensor support has a base portion with an essentially planar bottom surface configured to rest flat on the support layer, this means that the distance between the top surface and the bottom surface of the base portion continuously decreases towards the outer rim of the base portion. The base portion can have a circular footprint, i.e., a circular shape in a top or bottom view. These measures contribute to minimization of tactile disturbances of the occupant.

In some embodiments, the sensor support or one or more portions thereof have a substantially cylindrical shape with a longitudinal axis that is parallel to the surface normal of the active sensor surface. The active sensor surface can then be arranged on one of the end walls of the cylindrical portion of the sensor support. It is also conceivable that the sensor support has two substantially cylindrical portions whose cylinder axes are parallel, that the cylindrical portions are connected by a bridge portion, and that the active sensor surface is arranged in the bridge portion. The sensor support or one or more portions thereof may be configured to be received in one or more corresponding pre-shaped cavities in the support layer, the shape and lateral dimensions of the cavities preferably matching the shape and lateral dimensions of the corresponding portions of the sensor support, and the cavities being open towards the upper surface of the support layer that faces the cover.

The sensor support can itself have a modular construction. In particular, it can comprise a main body and a sensor carrier, the sensor carrier carrying the temperature and/or humidity sensor and being connected to the main body via a slide-in connection and/or a latching connection. In this case, there is a triple hierarchy of elements that are connected to one another: the smallest element is the sensor itself, including its integral packaging. This element is received in the sensor carrier, which in turn is received in the main body.

The packaging of the sensor itself can be connected to the sensor support (i.e., to the sensor carrier in the case of modular construction of the sensor support) by a variety of different methods, including adhesive bonding or pressing, by a latching connection etc.

The sensor module can further comprise at least one of the following components for signal processing and signal transmission:
  a connecting element for establishing an electrical connection with the temperature and/or humidity sensor; in this case, the connecting element preferably extends essentially perpendicular to the surface normal of the active sensor surface of the temperature and/or humidity sensor, i.e., essentially parallel to the air-permeable cover below the inside surface thereof, advantageously lying flat on the support layer; and
  a microcontroller.

The sensor module can comprise a communication device for wireless communication with a controller. The communication device can be, in particular, a Bluetooth™ device or a RFID transponder.

In another aspect, the present invention provides a seat assembly comprising a seat bottom and a backrest, at least one of the seat bottom and the backrest comprising a support layer and an air-permeable cover having an outside surface, which forms an occupant contact area of the seat assembly, and an inside surface that is directed towards the cushioning layer. The seat assembly further comprises a sensor module comprising a temperature and/or humidity sensor, which is disposed below the inside surface of the air-permeable cover. The sensor module is preferably constructed as described above. It can be secured to the support layer, to the air-permeable cover, or to another component of the seat assembly. If the sensor module is secured to the air-permeable cover, this can be done, for instance, by sewing. If the sensor module is secured to the support layer, this can be done, for instance, by the use of adhesive tape, of an adhesive layer, and/or by the use of mechanical anchors, as described above.

It is then preferred that the temperature and/or humidity sensor, in particular, the active sensor surface of the temperature and/or humidity sensor, is disposed at a distance of less than 25 mm, more preferably less than 10 mm, in particular less than 5 mm below the outside surface of the air-permeable cover. It is advantageous if the sensor module is disposed immediately below the outermost integral cover layer of the seat assembly. It is preferred that the sensor module is mounted in or on the support layer, e.g., by the use of adhesive and/or by the use of mechanical anchors, as discussed above.

In many cases, the support layer will be resiliently compressible. In order to further minimize tactile disturbances of the occupant, it is preferred that the sensor module is mounted in or on a portion of the support layer that faces the air-permeable cover, the sensor module being mounted in such a manner that at least a portion of the sensor module that extends into the support layer is movable relative to the support layer when the support layer is resiliently compressed. In other words, it is preferred that the sensor module can "float" in the support layer when the support layer is compressed, in order not to impede the compression of the support layer.

As already discussed above, it is preferred that the entire surface of the sensor module that faces the air-permeable cover is essentially flat and devoid of any prominent protrusions. It is preferred that the surface is domed, i.e., that the sensor module has a height above the surface of the support layer that continuously decreases towards the outer rim of the sensor module.

As already mentioned above, the support layer can define at least one pre-formed cavity that is open towards the air-permeable cover, and at least part of the sensor module can be disposed in the pre-formed cavity or cavities. In this case, it is preferred that at least part of the sensor module has a shape and dimensions that are complementary to the shape and dimensions of the pre-formed cavity, in order to avoid that the sensor module has lateral play in the cavity. In some embodiments, the pre-formed cavity can have a cylindrical shape, and at least part of the sensor module can then have a cylindrical shape with dimensions that match the dimensions of the pre-formed cavity.

As already discussed above, the sensor module can include a base portion that rests flat on the support layer. The base portion can then be fixedly connected to the support layer by the use of an adhesive, as discussed in more detail above. In addition or in the alternative, the sensor module can include one or more anchors that extend from the base portion into the support layer. In some embodiments, these anchors can pierce the support layer without the need of forming pre-formed cavities for the anchors, as discussed in more details above.

In alternative embodiments, the sensor module can be enclosed in an air-permeable bag, and the air-permeable bag can be sewn to the inside surface of the air-permeable cover or can be secured to the support layer, e.g., by stapling or by the use of adhesive tape.

Preferably the seat assembly is a vehicle seat assembly. In particular, the seat assembly may comprise structure for mounting the seat assembly to a vehicle body. For instance, the seat assembly may comprise structure for moving the seat assembly back and forth relative to the vehicle body to accommodate passengers of various sizes sitting on the seat bottom. The backrest may optionally be configured to pivot back and forth relative to the seat bottom. The vehicle may be, e.g., a car (the seat assembly forming a front or rear seat of the car), a truck, a bus, a train, an airplane etc. In other embodiments, the seat assembly is a seat for other purposes, e.g., for a theater, a movie theater, for medical or dental treatment, for an office, etc.

In order to provide a complete seat assembly with climate control, the seat assembly can further comprise at least one of a heating device, a cooling device and a ventilation device. The seat assembly can further comprise a controller configured to receive sensor signals from the sensor module and to control the heating device, cooling device and/or ventilation device based on the sensor signals. In such an automated climate seat, the need for the occupant to understand potentially overloaded human-machine interfaces is reduced. When used as the driver's seat in a vehicle, this contributes to safety because the driver is not disturbed or distracted by dealing with climate adaptations. Thermal comfort also influences safety by increasing the driver's attention span.

The seat assembly can further comprise a data communication device (e.g. an electrical data cable, a fiber-optic communication device or a wireless communication device like a Bluetooth™ adapter) for data exchange with a separate heating/ventilation/air conditioning (HVAC) system so as to provide the sensor signals to that system. The use of the humidity and temperature information in the HVAC system may in addition help to optimize regulation of that system to increase fuel economy. In particular, this helps to avoid that the driver and passengers overcompensate discomfort in the other direction with the result of unnecessary high energy consumption.

BRIEF DESCRIPTION OF THE DRAWINGS

Preferred embodiments of the invention are described in the following with reference to the drawings, which are for the purpose of illustrating the present preferred embodiments of the invention and not for the purpose of limiting the same. In the drawings.

DESCRIPTION OF PREFERRED EMBODIMENTS

Figure 1:
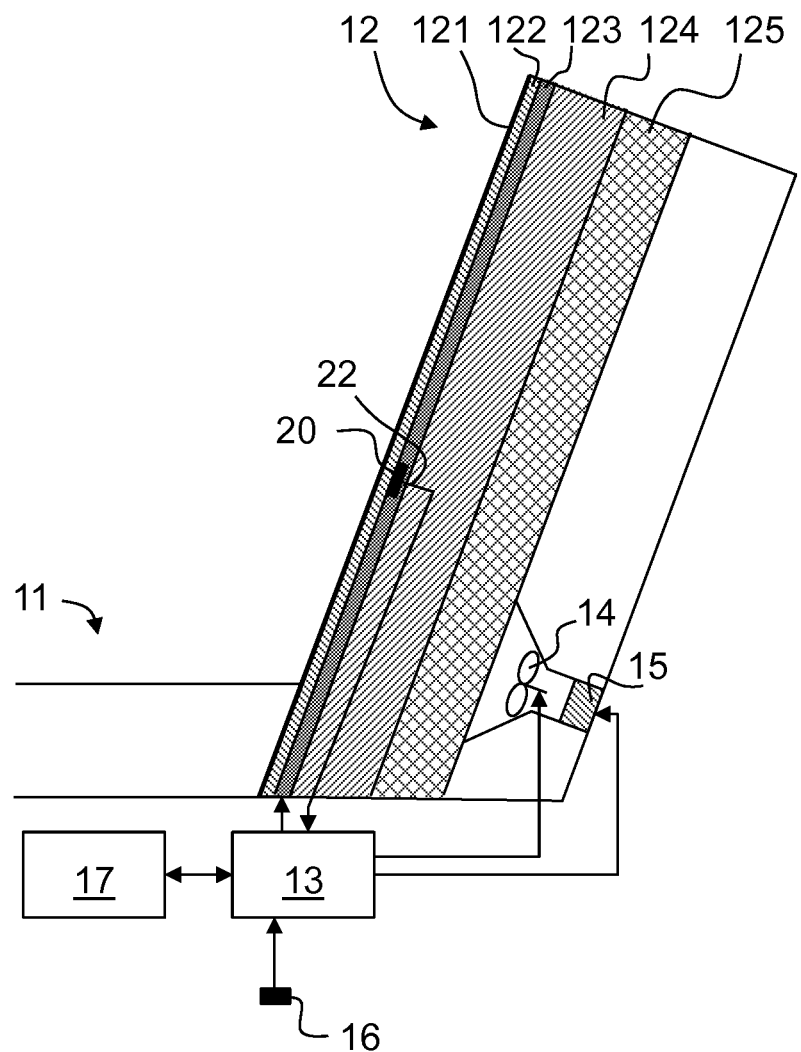
FIG. 1 shows, in a highly schematic manner, an air-conditioned vehicle seat in a longitudinal sectional view.
Figure 2:
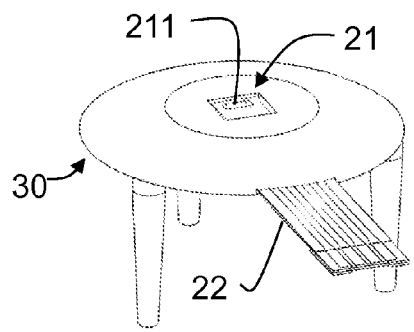
FIG. 2 shows, in a perspective view, a first embodiment of a sensor module.

FIG. 1 illustrates, in a highly schematic manner, an automated air-conditioned seat assembly. In the following, such a seat assembly will also be referred to as a "climate seat". The seat can be a vehicle seat, in particular, a front seat or a rear seat of a car. The seat assembly comprises a seat bottom 11 for supporting an occupant's buttocks, and a backrest 12 for supporting the occupant's back. The seat bottom 11 may comprise structure for attachment to a vehicle body. It may be configured to move back and forth relative to the vehicle body to accommodate passengers of different sizes sitting on the seat bottom 11. The backrest 12 is coupled to the seat bottom 11 and is arranged to extend in a generally upward direction away from the seat bottom 11. The backrest 12 may be configured to pivot back and forth relative to the seat bottom 11.

Only the backrest 12 is illustrated in more detail. The drawing is not to scale. The backrest 12 comprises, from the outside to the inside, an air-permeable cover 121, for instance, a thin sheet of perforated leather. An integral backing layer 122, e.g., a thin, air-permeable foam backing, can optionally be laminated to the air-permeable cover 121. The air-backing layer 122 is optionally followed by a thin, air-permeable heating mat 123, which in turn is followed by an air-permeable foam or fiber layer 124. The foam or fiber layer 124 will generally be resiliently compressible to provide comfort to the occupant. Below the foam or fiber layer 124, an air distribution layer 125 or spacer layer is disposed, comprising a plurality of air conduits (not illustrated). A ventilation system comprising a fan 14 forces air through the air distribution layer 125, the foam or fiber layer 124, the heating mat 123, the backing layer 122 and the air-permeable cover 121 to the occupant. The air can be pre-cooled or pre-heated by a heating and/or cooling element 15, e.g., a Peltier element. The ventilation system creates a stream of air around the occupant of the seat to provide a seat-specific climate.

A sensor module 20 comprising a combined temperature and humidity sensor is disposed below the air-permeable cover 121. In the present example, the sensor module 20 is arranged in/on the heating mat 123. However, the sensor module may instead be arranged in/on the backing layer 122 or in/on the foam or fiber layer 124. It may be preferable to thermally decouple the sensor module 20 from the heating mat 123, e.g., by providing a cutout in the heating mat, or by arranging the sensor module in a zone of the heating mat that is not actively heated. In general terms, the sensor module 20 is mounted on or in a support layer that directly or indirectly supports the air-permeable cover 111.

The combined temperature and humidity sensor of the sensor module 20 records temperature and humidity data that reflect the physiological state of the seat's occupant. The sensor may be a semiconductor sensor. Such sensors are widely available commercially. For instance, the sensor may be a sensor of the SHT series available from Sensirion AG, Stäfa, Switzerland.

Data from the sensor module 20 are fed to a control unit 13 through a connecting element 22 of the sensor module 20. The control unit 13 runs an algorithm to automatically control the speed of the fan 14, the heating/cooling power of the heating/cooling element 15 and the heating power of the heating mat 123, based on the signals from the sensor module 20. This enables continuous, stepless control of the seat-specific climate. Control can be fully automatic, leading to increased safety since the driver does not need to be concerned with manually adjusting the settings of the heating or cooling power and of the speed of the fan. The control unit 13 may include a compensation and acceleration engine, i.e., an algorithm that extrapolates physiological parameters from the sensor data and provides improved control signals for accelerating control. The algorithm that is executed in the control unit 13 may take into account signals from further sensors 16, such as further temperature and/or humidity sensors for measuring the temperature/humidity of ambient air inside and/or outside the vehicle cabin, or occupant detection sensors (including weight sensors). The control unit 13 can further be coupled to the vehicle's general heating, ventilation and air conditioning (HVAC) system 17. Humidity and temperature information obtained from the sensor module 20 may be provided to the HVAC system 17 and/or to other systems of the vehicle. The data may be logged and/or visualized on a display of the vehicle.

The control unit 13 may be configured to receive user-specific data, such as height, weight, gender, and/or user preferences. The control unit may be configured to store such user-specific data in a memory and to retrieve such data from the memory. User-specific data may, for instance, be entered manually into the control unit, may be received from the vehicle's general heating, ventilation and air conditioning (HVAC) system 17, may be coded in a car key and read from the key when the car is started, and/or may be provided through a portable electronic device such as a smartphone.

In other embodiments, the climate seat may lack its own active cooling or heating components, but may use air from the global air conditioning system instead to air condition the seat. In this case, the humidity and temperature signal may be processed in the control unit of the general HVAC system 17, and the control unit 13 can be left away.

When an occupant sits on the seat, moisture (humidity) and temperature are exchanged with the seat. In order to achieve fast response times without causing tactile disturbances to the occupant, the sensor module 20 is disposed below the air-permeable cover 121, at a distance of only a few millimeters from the outside surface of the air-permeable cover 121. By anchoring the sensor module 20 in a support layer that is close to the air-permeable cover 121, fast response times are achieved, as the moisture transfer path is short and good temperature coupling against the back of a person can be expected.

A similar setup can be chosen for the seat bottom 11. If sensors, ventilation components, heating components and/or cooling components are present in the seat bottom 11, these components can be interfaced with the control unit 13 as well.

Many modifications of the setup of the seat assembly are possible without leaving the scope of the present invention. In particular, other sequences of layers are conceivable. The seat assembly may serve a different purpose than for installation in a vehicle. For instance, the seat assembly may be installed in a theater or in any other environment in which a climate seat may be desirable. The actual setup of the seat will consequently depend on the purpose for which the seat is designed.

Figure 3:
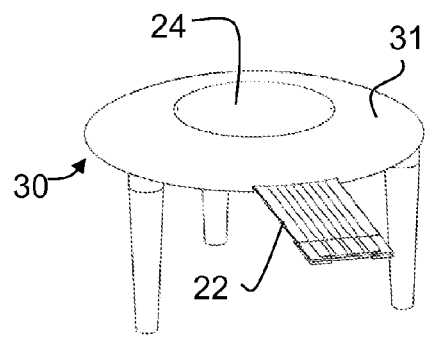
FIG. 3 shows, in a perspective view, the sensor module in FIG. 2 with a membrane that covers the active sensor surface.
Figure 4:
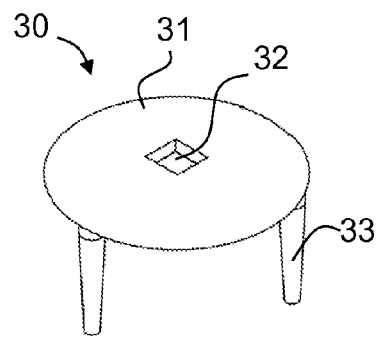
FIG. 4 shows the sensor support of the sensor module in FIG. 2, in a perspective view.
Figure 5:
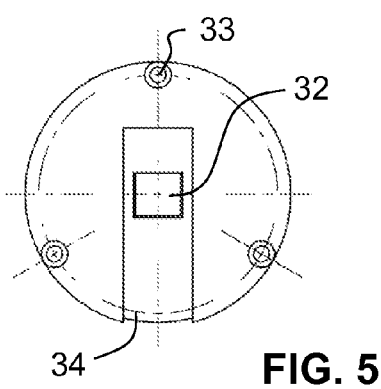
FIG. 5 shows the sensor support in FIG. 3 in a bottom view.

FIGS. 2-7 illustrate a first embodiment of a sensor module for use in a climate seat of the type described above. The sensor module comprises a temperature and humidity sensor 21, which is provided with a connecting element 22 in the form of a flat, flexible printed circuit board ("flexprint connector"). The sensor 21 and the connecting element 22 are together mounted, e.g., glued, to the bottom of a sensor support 30 for mechanically supporting the sensor 21 when it is mounted in the seat assembly. The sensor support 30 comprises a flat, domed base portion 31 defining a rectangular window 32, and a plurality of legs (here: three legs) 33 extending downward from the bottom of the base portion 31. On the bottom of the base portion 31, a notch 34 is formed for receiving the sensor 21 and the connecting element 22. This notch is laterally open towards one side of the sensor support 30 to allow the connecting element 22 to extend beyond the rim of the base portion 31 in a direction that is perpendicular to the direction of the legs 33. The sensor 21, the connecting element 22 and the bottom of base portion 31 together form an essentially planar bottom surface when the sensor 21 and the connecting element 22 are connected to the sensor support 23. The sensor 21 has an active sensor surface 211, in particular, a humidity-sensitive polymer layer on a semiconductor substrate for measuring humidity, which is accessible to media through a window-like opening in the packaging of the sensor 21, this window-like opening being arranged directly below the window 32. The window 32 can be covered with a thin protective membrane 24 to protect the active sensor surface 211 from dirt and liquids that might inadvertently reach the sensor module. As illustrated in FIG. 3, the protective membrane 24 can be glued to the top surface of the base portion 31.

Figure 6:
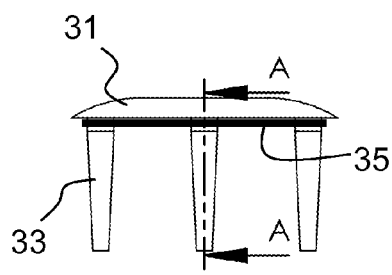
FIG. 6 shows the sensor support in FIG. 3 in a side view.
Figure 7:
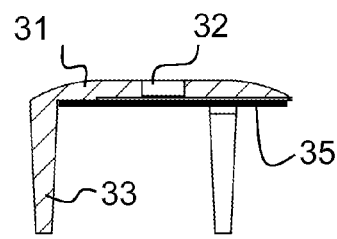
FIG. 7 shows the sensor support in FIG. 3 in a sectional view in plane A-A as indicated in FIG. 5.
Figure 8:
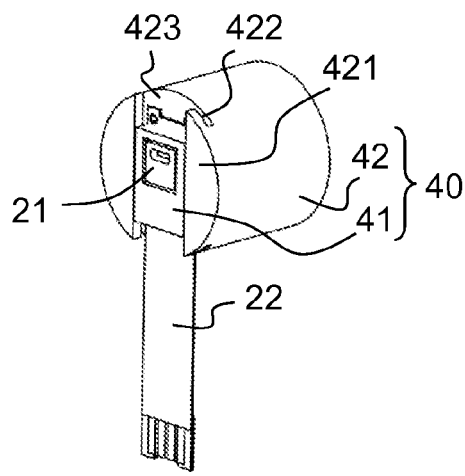
FIG. 8 shows, in a perspective view, a second embodiment of a sensor module.
Figure 9:
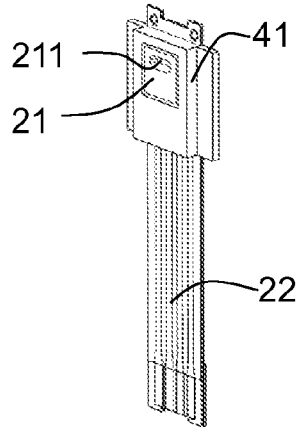
FIG. 9 shows a sub-unit of the sensor module in FIG. 8.
Figure 10:
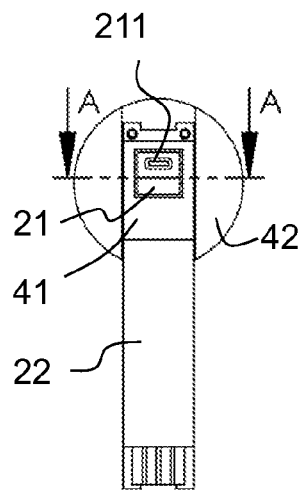
FIG. 10 shows the sensor module in FIG. 8 in a top view.

In use, the sensor module is anchored in a support layer of a seat assembly (e.g., in the heating mat 123 as described above) by simply pressing the legs 33 into the support layer. In other words, the legs 33 act as anchors for the sensor module. In order to improve retention in the support layer, the base portion 31, which rests flat on the surface of the support layer, may be glued to the support layer. To this end, the bottom surface of the base portion 31 may be provided with a double-sided adhesive tape 35 as illustrated in FIGS. 6 and 7, or with another kind of adhesive layer, which may be protected before use by a removable protective layer.

The surface of the sensor module that is directed away from the support layer is covered by the air-permeable cover of the seat assembly, as described above. This surface has a domed shape and is essentially flat and devoid of any protrusions, in order to minimize tactile disturbances of the occupant of the seat assembly. When pressure is exerted to the domed surface, the support layer of the seat assembly may be resiliently compressed by the pressure. When this happens, the rigid legs 33, which extend into the support layer, are free to move axially ("float") within the support layer so as not to impede compression of the support layer. In all situations, the flexible connecting element 22 will remain lying flat on the support layer. All these measures further minimize tactile disturbances of the occupant.

A second embodiment of a sensor module is illustrated in FIGS. 8-12. The sensor module again comprises a temperature and/or humidity sensor 21 and a connecting element 22, as in the first embodiment. These components are mounted in a modular sensor support 40. The sensor support 40 comprises a flat sensor carrier 41, which in turn is mounted in a cylindrical main body 42 by a slide-in connection. To this end, the main body 42 has a notch 423 delimited by walls 421 in which slots 422 are formed. The sensor carrier 41 has a shape that is complementary to the notch 423 and the slots 422. Thereby it is possible to laterally slide the sensor carrier 41, complete with the sensor 21 and the connecting element 21, into the notch 423 and the slots 422, to connect the sensor carrier 41 to the main body 42. Once the sensor carrier 41 has been slid into the main body 42, it is retained therein by a latching connection (not illustrated). The sensor carrier 41 provides a certain degree of mechanical protection to the sensor 21, forming a window through which the active sensor surface 211 is accessible. Further protection is provided by the main body 42, which in addition simplifies fixation in a support layer.

Figure 13:
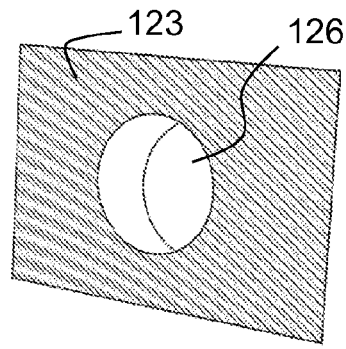
FIG. 13 shows a support layer of a vehicle seat with a pre-formed cavity therein.

In use, the main body 42 of the sensor module is disposed in a pre-formed cavity of a support layer, which has a shape that is complementary to the shape of the main body 42. Such a cavity is illustrated, by the way of example, in FIG. 13. In this example, a cylindrical cavity 126 is formed in the heating mat 123. The diameter of the cavity 126 matches the diameter of the main body 42. In this way, the main body 42 can be received in the cavity 126 without lateral clearances and consequently without lateral play. However, while the position of the main body 42 is fixed laterally, the main body is still allowed to "float" axially (along its cylinder axis) within the support layer when the support layer is compressed, while the flexible connecting element 22 remains lying flat on the support layer, so as to minimize tactile disturbances of the occupant.

In a modification, the sensor module can comprise a microcontroller 18 and/or a communication module 19 for wireless communication with a control unit, e.g., a Bluetooth™ module or an RFID transponder, and/or an energy source, e.g. a rechargeable or disposable battery. These components can be easily mounted within the main body 42.

Figure 11:
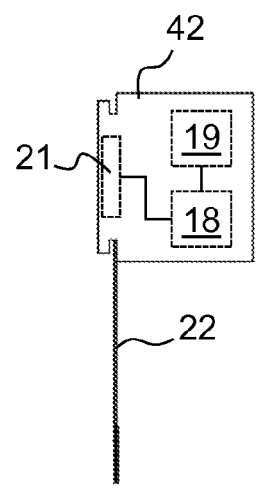
FIG. 11 shows the sensor module in FIG. 8 in a front view.
Figure 12:
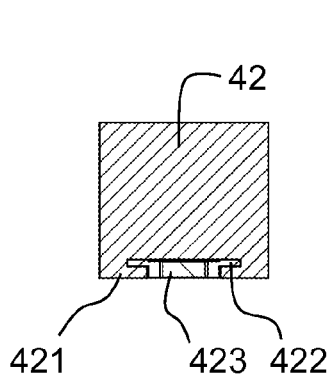
FIG. 12 shows the sensor module in FIG. 8 in a side view.

This is schematically illustrated in FIG. 11. In this case, the connecting element 22 may be left away. In this manner, a fully autonomous sensor module is obtained, which can be integrated into a seat assembly without complicated cabling.

Figure 14:
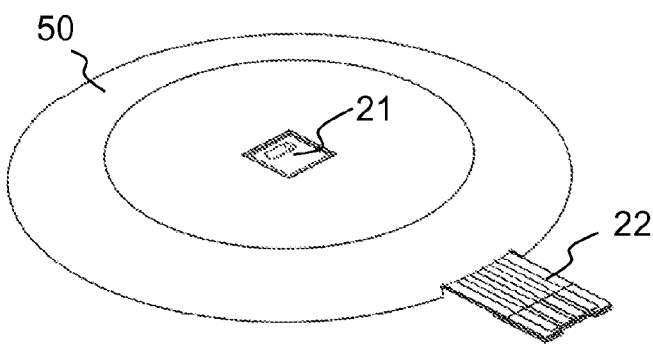
FIG. 14 shows, in a perspective view, a third embodiment of a sensor module.

FIG. 14 illustrates a third embodiment of a sensor module. The sensor module has a similar setup as in the first embodiment (sensor 21, connecting element 22, domed sensor support 50 forming a window); however, it lacks legs for anchoring the sensor module in the support layer. Instead, the sensor support is simply glued to the surface of the support layer. As discussed in conjunction with the first embodiment, a double-sided adhesive tape or any other kind of adhesive layer may be employed to this end.

Figure 15:
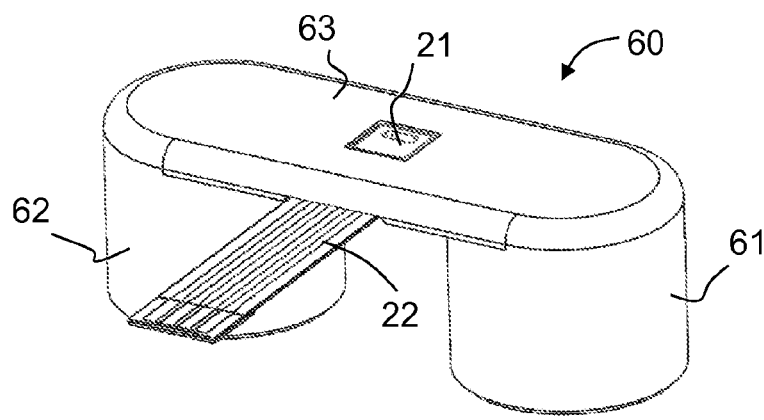
FIG. 15 shows, in a perspective view, a fourth embodiment of a sensor module.

FIG. 15 illustrates a fourth embodiment of a sensor module. The sensor 21 with connecting element 22 is mounted on a sensor support 60 that has two cylindrical anchor portions 61, 62 interconnected by a flat bridge portion 63. The sensor 21 is disposed below a window in the bridge portion 63. The bridge portion 63, the sensor 21 and the connecting element 22 together form an essentially planar bottom surface. The bridge portion 63 can thus be understood to form the base portion of the sensor support in the sense as it is described above, from which the anchor portions 61, 62 extend downwards. In use, the anchor portions 61, 62 extend into two identical pre-formed cavities in the support layer of the seat assembly, while the bridge portion 63 lies flat on the surface of the support layer. This embodiment is advantageous in that it provides additional space for further electronic components such as microcontrollers, communications modules etc. within the anchor portions 61, 62.

Figure 16:
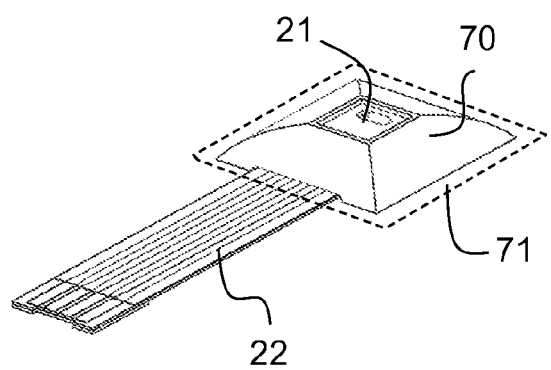
FIG. 16 shows, in a perspective view, a fifth embodiment of a sensor module.

A fifth embodiment of a sensor module is illustrated in FIG. 16. The sensor 21 with connecting element 22 is mounted in a relatively small sensor support 70 forming a window, which in turn is enclosed in a small air-permeable bag 71, the dimensions of the bag 71 roughly matching the dimensions of the sensor support 70, and the connecting element 22 extending to the outside of the bag 71. In use, this bag 71 is sewn to the inside surface of the air-permeable cover of the seat assembly.

Figure 17:
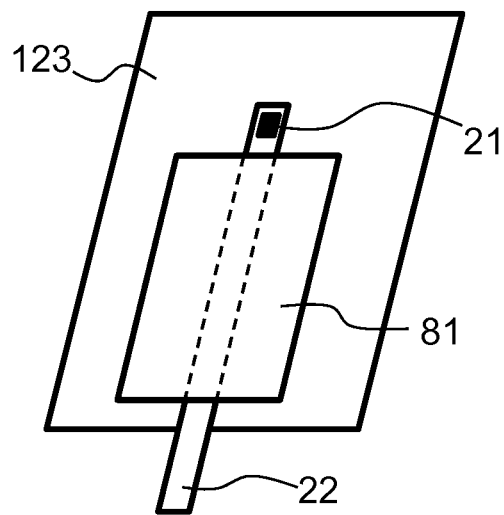
FIG. 17 shows, in a highly schematic perspective view, a sixth embodiment of a sensor module.

FIG. 17 illustrates a sixth embodiment of a sensor module. Here, the sensor module is formed by the sensor 21 with attached connecting element 22 alone, i.e., no separate sensor support is provided. The sensor module is attached to the heating mat 123, to any other kind of support layer or to the inside surface of the air-permeable cover with the aid of an adhesive tape 81.

Figure 18:
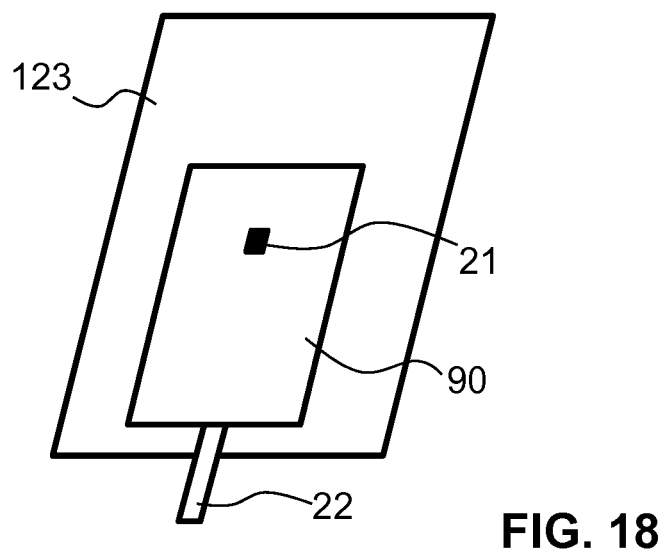
FIG. 18 shows, in a highly schematic perspective view, a seventh embodiment of a sensor module.

FIG. 18 illustrates a seventh embodiment of a sensor module. In this embodiment, the sensor 21 with attached connecting element 22 is mounted on a rectangular, flexible sensor support 90 forming a window for access to the active sensor surface, which in turn is glued to the heating mat 123, to any other kind of support layer or to the inside surface of the air-permeable cover.

Most of the above-discussed exemplary embodiments can be present within the seat assembly or can be left away at the will of the seat manufacturer, without influencing the general setup or outer appearance of the seat assembly. This simplifies the management of different configurations of the seat assembly by the seat manufacturer.

It is apparent that a large number of modifications of the above-discussed exemplary embodiments are possible without leaving the scope of the present invention. In particular, a protective membrane, as discussed in conjunction with the first embodiment, can be provided in all embodiments. In all embodiments, the sensor support may have a modular construction with a sensor carrier and a separate main body, as discussed in conjunction with the second embodiment. In all embodiments, the sensor module may be attached to the support layer with the use of adhesive. All embodiments may include an integrated microcontroller 18 and/or a communication module 19 for wireless communication, as discussed in conjunction with the second embodiment. Such components can readily be integrated into the sensor support. Whereas specific shapes of the sensor support have been described in conjunction with the exemplary embodiments, other shapes are possible. Whereas a specific type of sensor has been described conjunction with the exemplary embodiments, other kinds of sensors can be employed, in particular, sensors with other kinds of packaging. Other kinds of connecting elements than discussed in conjunction with the exemplary embodiments can be used, and the connecting elements can be arranged differently. For instance, the connecting element can be a cable that extends in an arbitrary direction from the sensor itself. A great many other modifications are possible. All elements that have been discussed in conjunction with one specific embodiment can be combined with the elements of any of the other embodiments without leaving the scope of the present invention.

The invention claimed is:

1. A sensor module for integration within a seat assembly comprising a seat bottom and a backrest, at least one of the seat bottom and the backrest comprising a support layer and an air-permeable cover having an outside surface, which forms an occupant contact area of the seat assembly, and an inside surface, the sensor module comprising:
   a combined temperature and humidity sensor; and
   a separate sensor support for mechanically supporting the combined temperature and humidity sensor, the sensor support being configured to be arranged on or in the support layer below the air-permeable cover, wherein the combined temperature and humidity sensor comprises a semiconductor-based humidity sensor, the semiconductor-based humidity sensor comprising a semiconductor substrate and a polymer layer disposed on the semiconductor substrate, and wherein the polymer layer forms an active sensor surface.

2. The sensor module of claim 1, wherein the sensor support defines a window that is fully surrounded by material of the sensor support, and wherein the active sensor surface is accessible for media through the window.

3. The sensor module of claim 2, wherein the sensor module comprises an air-permeable protective membrane that covers the window.

4. The sensor module of claim 1, wherein the sensor support includes a base portion having an essentially planar bottom surface configured to rest flat on the support layer.

5. The sensor module of claim 4, wherein the base portion has a generally flat configuration.

6. The sensor module of claim 5, wherein the base portion has a top surface configured to face away from the support layer towards the air-permeable cover, the entire top surface of the base portion being devoid of any prominent protrusions.

7. The sensor module of claim 6,
   wherein the base portion has an outer rim, the top surface and the bottom surface meeting at the outer rim, and
   wherein the top surface is domed, a distance between the top surface and the bottom surface of the base portion continuously decreasing towards the outer rim until the top surface and the bottom surface meet at the outer rim.

8. The sensor module of claim 4, wherein the combined temperature and humidity sensor is mounted to the bottom surface of the base portion.

9. The sensor module of claim 4, further comprising a connecting element for establishing an electrical connection with the combined temperature and humidity sensor, the connecting element comprising a flat, flexible printed circuit board,
   wherein the combined temperature and humidity sensor and the connecting element are together mounted to the bottom surface of the base portion.

10. The sensor module of claim 9,
    wherein the base portion has an outer rim,
    wherein the sensor support includes one or more anchors configured to extend from the base portion into the support layer when the base portion rests flat on the support layer, the anchors extending along a longitudinal direction, and
    wherein the connecting element extends beyond the outer rim of the base portion in a direction that is perpendicular to the longitudinal direction.

11. The sensor module of claim 9, wherein the base portion has a notch, the notch receiving the combined temperature and humidity sensor and the connecting element.

12. The sensor module of claim 11,
    wherein the base portion has an outer rim, and
    wherein the notch is laterally open towards one side of the sensor support so as to allow the connecting element to extend beyond the outer rim of the base portion.

13. The sensor module of claim 9, wherein the base portion, the combined temperature and humidity sensor, and the connecting element together form a planar bottom surface.

14. The sensor module of claim 4, wherein the sensor module comprises an adhesive layer on the bottom surface of the base portion.

15. The sensor module of claim 14, wherein the adhesive layer is covered by a peelable protective layer.

16. The sensor module of claim 4, wherein the sensor support includes one or more anchors configured to extend from the base portion into the support layer when the base portion rests flat on the support layer.

17. The sensor module of claim 1, wherein the sensor module has a top surface configured to face away from the support layer towards the air-permeable cover, the entire top surface being devoid of any prominent protrusions.

18. The sensor module of claim 17, wherein the top surface is domed.

19. The sensor module of claim 1 wherein the sensor support comprises a main body and a sensor carrier, the sensor carrier carrying the combined temperature and humidity sensor and being connected to the main body via a slide-in connection and/or a latching connection.

20. The sensor module of claim 1, wherein the sensor module comprises at least one of:

a connecting element for establishing an electrical connection with the combined temperature and humidity sensor; and a microcontroller.

21. The sensor module of claim 1, wherein the sensor module comprises a communication device for wireless communication with a remote control unit.

22. A seat assembly comprising a seat bottom and a backrest, at least one of the seat bottom and the backrest comprising:

a support layer, an air-permeable cover having an outside surface, which forms an occupant contact area of the seat assembly, and an inside surface that is directed towards the support layer; and a sensor module comprising a combined temperature and a separate sensor support for mechanically supporting the combined temperature and humidity sensor, the sensor support being configured to be arranged on or in the support layer below the air-permeable cover, wherein the sensor module is disposed below the inside surface of the air-permeable cover, wherein the combined temperature and humidity sensor comprises a semiconductor-based humidity sensor, the semiconductor-based humidity sensor comprising a semiconductor substrate and a polymer layer disposed on the semiconductor substrate, and wherein the polymer layer forms an active sensor surface.

23. The seat assembly of claim 22, wherein the combined temperature and humidity sensor is disposed at a distance of less than 25 mm below the outside surface of the air-permeable cover.

24. The seat assembly of claim 22, wherein the sensor module is mounted in or on the support layer.

25. The seat assembly of claim 24, wherein the support layer is a heating mat.

26. The seat assembly of claim 24, wherein the support layer is resiliently compressible, and wherein the sensor module is mounted in or on a portion of the support layer that faces the air-permeable cover, the sensor module being mounted in such a manner that at least a portion of the sensor module that extends into the support layer is movable relative to the support layer when the support layer is resiliently compressed.

27. The seat assembly of claim 22, wherein the support layer defines at least one pre-formed cavity that is open towards the air-permeable cover, and wherein at least part of the sensor module is disposed in the at least one pre-formed cavity.

28. The seat assembly of claim 22, wherein the sensor module is enclosed in an air-permeable bag.

29. The seat assembly of claim 22, further comprising at least one of a heating device, a cooling device and a ventilation device, and comprising a controller being configured to receive sensor signals from the sensor module and to control the heating device, cooling device and/or ventilation device based on the sensor signals.

30. The seat assembly of claim 22, wherein the sensor module comprises a separate sensor support for mechanically supporting the combined temperature and humidity sensor, the sensor support being arranged on or in the support layer below the air-permeable cover.

31. The seat assembly of claim 30, wherein the support layer is a heating mat.

32. The seat assembly of claim 30, wherein the sensor support includes a base portion having an essentially planar bottom surface, the bottom surface resting flat on the support layer, and wherein the sensor support includes one or more anchors, the anchors extending from the base portion into the support layer.

33. The seat assembly of claim 32, wherein the anchors protrude from the bottom surface of the base portion along a longitudinal direction.

34. The seat assembly of claim 33, wherein the anchors are free to move within the support layer along the longitudinal direction when the support layer is resiliently compressed.

35. A sensor module for integration within a seat assembly comprising a seat bottom and a backrest, at least one of the seat bottom and the backrest comprising a support layer and an air-permeable cover having an outside surface, which forms an occupant contact area of the seat assembly, and an inside surface, the sensor module comprising:

a combined temperature and humidity sensor; and a separate sensor support for mechanically supporting the combined temperature and humidity sensor, the sensor support being configured to be arranged on or in the support layer below the air-permeable cover, wherein the sensor support defines a window that is fully surrounded by material of the sensor support, and wherein the combined temperature and humidity sensor has an active sensor surface that is accessible for media through the window, wherein the combined temperature and humidity sensor comprises a packaging, the packaging providing a first contribution to mechanical protection of the combined temperature and humidity sensor, the packaging defining a window-like opening, wherein the sensor support provides a second contribution to mechanical protection of the combined temperature and humidity sensor, wherein the active sensor surface is disposed below the window-like opening, and wherein a diffusion path exists between the window of the sensor support and the window-like opening of the packaging.

36. The sensor module of claim 35, wherein the window of the sensor support and the window opening of the packaging are arranged on top of one another.

37. The sensor module of claim 1, wherein the active sensor surface faces the inside surface of the air-permeable cover.

* * * * *